United States Patent [19] [11] 4,082,755
van Wijngaarden et al. [45] Apr. 4, 1978

[54] 1-[(DIARYLMETHYL)AMINOALKYL]-PIPERIDIMES

[75] Inventors: Ineke van Wijngaarden; Willem Soudijn, both of Oud-Turnhout; Jan Vandenberk, Beerse; Jozef Fr. Hens, Nijlen, all of Belgium

[73] Assignee: Janssen Pharmaceutica N.V., Beerse, Belgium

[21] Appl. No.: 768,527

[22] Filed: Feb. 14, 1977

[51] Int. Cl.$^2$ ............................................. C07D 401/04
[52] U.S. Cl. ........................... 260/293.6; 260/239 E; 260/293.66; 260/293.78; 260/293.83; 260/293.84; 260/456 A; 260/570 R
[58] Field of Search ........... 260/293.6, 293.66, 293.83, 260/293.84, 293.78

[56] References Cited

U.S. PATENT DOCUMENTS

| 2,937,180 | 5/1960 | Janssen | 260/293.84 |
| 4,017,624 | 4/1977 | Marvyama | 260/293.6 |
| 4,031,226 | 6/1977 | Soudijn | 260/293.6 |

FOREIGN PATENT DOCUMENTS

| 1,102,183 | 2/1968 | United Kingdom | 546/223 |

Primary Examiner—Henry R. Jiles
Assistant Examiner—Richard A. Schwartz
Attorney, Agent, or Firm—Salvatore R. Conte

[57] ABSTRACT

Novel compounds of the class of 1-[(diarylmethyl)aminoalkyl]piperidines having neuroleptic activity.

5 Claims, No Drawings

1-[(DIARYLMETHYL)AMINOALKYL]-PIPERIDIMES

BACKGROUND OF THE INVENTION:

In the prior art there may be found a number of 1-(diarylalkyl)- and 1-(aminoalkyl)piperidine derivatives having neuroleptic properties. Such compounds are described, for example, in U.S. Pat. Nos. 3,575,990, 3,238,216, 3,196,157 and Brit. Pat. No. 1,448,781.

The compounds of this invention differ from the foregoing essentially by the nature of the (diarylmethyl)aminoalkyl group present in the 1-position of the piperidine group.

DESCRIPTION OF THE PREFERRED EMBODIMENTS:

This invention relates to novel chemical compounds and more particularly to a novel series of 1-[(diarylmethyl)aminoalkyl]piperidines having the formula:

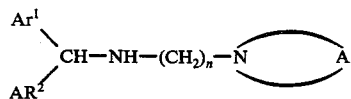

and the pharmaceutically acceptable acid addition salts thereof, wherein:

Ar$^1$ and Ar$^2$ are each independently selected from the group consisting of phenyl and substituted phenyl, said substituted phenyl being phenyl having from 1 to 2 substituents independently selected from the group consisting of halo, lower alkyl, lower alkyloxy and trifluoromethyl;

$n$ is the integer 2 or 3; and the radical

is a member selected from the group consisting of the following:

a. a radical of the formula

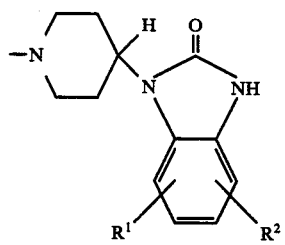

wherein R$^1$ and R$^2$ are each independently selected from the group consisting of hydrogen, halo, lower alkyl and lower alkyloxy;

b. a radical of the formula

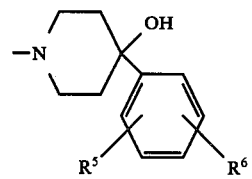

wherein R$^3$ and R$^4$ are each independently selected from the group consisting of hydrogen, halo, lower alkyl, lower alkyloxy and trifluoromethyl; and c. a radical of the formula

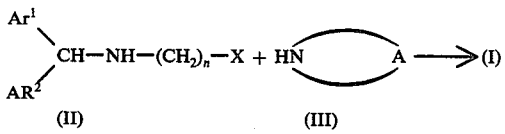

wherein R$^5$ is selected from the group consisting of hydrogen and methyl; and R$^6$ is selected from the group consisting of hydrogen, halo, lower alkyl and trifluoromethyl.

As used in the foregoing and in the following definitions, the term "lower alkyl" is meant to include straight and branch chained hydrocarbon radicals having from 1 to 5 carbon atoms such as, for example, methyl, ethyl, 1-methylethyl, 1,1-dimethylethyl, propyl, 1-methylpropyl, butyl, pentyl and the like; and the term "halo" is generic to halogens of atomic weight less than 127, i.e., fluoro, chloro, bromo and iodo.

The compounds of formula (I) can generally be prepared by the reaction of an appropriate reactive ester of formula (II) with an appropriate piperidine derivative of formula (III) following standard N-alkylating procedures.

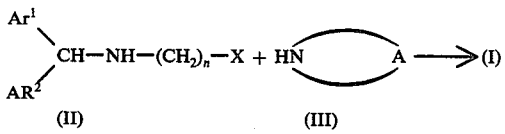

Ar$^1$, Ar$^2$ and $n$ as they appear in formula (II) have the same meaning as assigned to them previously, while X represents an appropriate reactive ester residue such as, for example, halo, preferably chloro or bromo; or a sulfonyloxy group, e.g., methylsulfonyloxy or 4-methylphenylsulfonyloxy. The radical

in formula (III) has the previously indicating meaning.

The foregoing N-alkylation reaction is preferably conducted in an appropriate reaction-inert organic solvent, such as, for example, a lower alkanol, e.g., methanol, ethanol, propanol, butanol and the like; a ketone, e.g., 4-methyl-2-pentanone; an ether, e.g., 1,4-dioxane, 1,1'-oxybisethane and the like; N,N-dimethylformamide; nitrobenzene and the like; or a mixture of such solvents.

In order to pick up the acid which is liberated during the course of the reaction it is appropriate to add to the reaction mixture an appropriate base such as, for example, an alkali metal carbonate or hydrogen carbonate. In some instances it may be advantageous to add a small amount of an appropriate iodide salt, preferably an alkali metal iodide, as a reaction promotor. Somewhat elevated temperatures are appropriate to enhance the reaction rate and most preferably the reaction is carried out at the reflux temperature of the reaction mixture.

In this and following preparations the reaction products are separated from the mixture, and, if necessary, further purified by the application of methodologies which are generally known in the art.

Compounds of formula (I) wherein $n$ is 2, (I-a), may also be obtained by the reaction of (III) with an aziridine of formula (IV) wherein $Ar^1$ and $Ar^2$ are as previously defined.

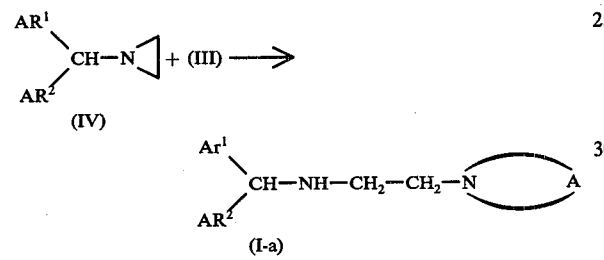

Said reaction may conveniently be carried out by stirring the reactants together, preferably while heating and most preferably under reflux, in an appropriate reaction-inert organic solvent. In general the same solvents as described hereabove in connection with the synthesis of compounds (I) starting from (II) and (III) may be employed.

The starting materials of formula (II), a number of which are known compounds, may all be prepared following methodologies known in the art. For example, such compounds are easily obtained by the reaction of an appropriate reactive ester of formula (V) wherein $Ar^1$, $Ar^2$ and X are as previously defined, with an appropriate aminoalkanol of formula (VI) wherein $n$ has the same meaning as indicated hereinabove, followed by the conversion of the hydroxyl group of the thus obtained intermediate (VII) into a reactive ester group.

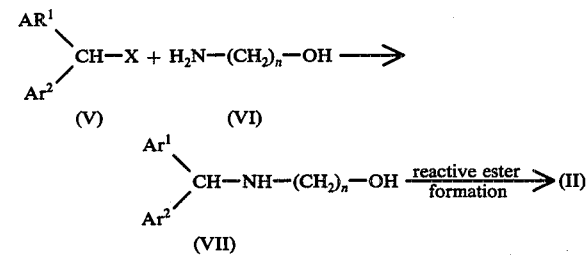

The reaction of (V) with (VI) may be carried out in an analogous manner as described above for the preparation of compounds (I) starting from (II) and (III).

The conversion of (VII) into a reactive ester (II) may be accomplished by the application of art-known methods of preparing reactive esters from alcohols. In the preparation of halides there may be used common halogenating agents such as hydrohalic acid, e.g., hydrochloric or hydrobromic acid; or other halogenating agents, e.g., sulfinyl chloride. Methanesulfonates and 4-methylbenzenesulfonates are conveniently prepared by the reaction of (VII) with respectively methanesulfonyl chloride or 4-methylbenezenesulfonyl chloride.

The precursor reactive esters of formula (V) herein are generally known and may all be prepared following art-known procedures, for example, by converting the corresponding diarylmethanol into a reactive ester according to procedures previously described herein.

Aziridines of formula (IV) can be derived from the corresponding reactive esters of formula (II) wherein $n$ is 2 by treating the latter with alkali.

The piperidine derivatives of formula (III) are generally known compounds. Such compounds and methods of preparing the same are described, for example, in U.S. Pat. Nos. 3,910,930, 3,989,707, 3,155,670, 3,438,991, 3,518,276, 3,575,990 and 3,714,151.

The compounds of this invention may be converted to their therapeutically useful acid addition salts by treatment with an appropriate acid, such as, for example, an inorganic acid, such as hydrohalic acid, e.g., hydrochloric, hydrobromic and the like, and sulfuric acid, nitric acid, phosphoric acid and the like; or an organic acid, such as, for example, acetic, propanoic, 2-hydroxyacetic, 2-hydroxypropanoic, 2-oxopropanoic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, benzoic, 3-phenyl-2-propenoic, α-hydroxybenzeneacetic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) and the pharmaceutically acceptable acid addition salts thereof were found to be potent neuroleptics and as such they can be used as tranquilizing agents, for example, in the treatment of various forms of mental illness.

The useful neuroleptic properties of the compounds (I) are clearly evidenced by the experimental data given hereafter.

Neuroleptic drugs are known to inhibit emesis induced by apomorphine in dogs. The compounds listed in tables I and II were administered either subcutaneously or orally to a minimum of a group of 3 beagle dogs. The animals were challenged 1, 4 or 16 hours after subcutaneous administration or 4 hours after oral administration with a standard dose of 0.31 mg/kg of apomorphine hydrochloride (subcutaneously). This high dose of apomorphine induces emesis in all untreated dogs.

Tables I and II give the $PD_{50}$-values (in mg/kg subcutaneously or orally), i.e., the dose of the compound protecting at the stated time half of the animals from emesis. The compounds listed therein are not given for the purpose of limiting the invention thereto but only to exemplify the useful properties of all the compounds within the scope of formula I.

TABLE I

Compounds of the formula:

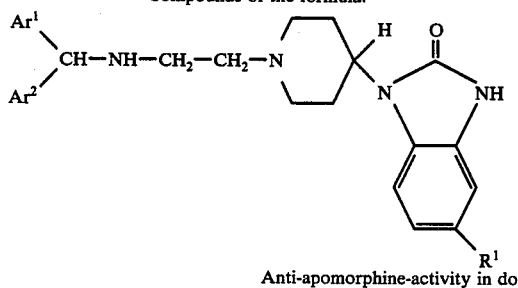

| Ar¹ | Ar² | R¹ | 1 hour s.c. | 4 hours s.c. | 16 hours s.c. | 4 hours oral |
|---|---|---|---|---|---|---|
| $C_6H_5$ | 4-$CH_3$—$C_6H_4$ | H | 0.06 | 0.25 | 0.5 | 1.5 |
| $C_6H_5$ | 3-$CF_3$—$C_6H_4$ | H | — | — | — | 2.5 |
| 4-Cl—$C_6H_4$ | 4-Cl—$C_6H_4$ | H | — | — | — | 2.0 |
| $C_6H_5$ | 3-Cl—$C_6H_4$ | Cl | — | — | — | 2.5 |
| $C_6H_5$ | 4-$CH_3$—$C_6H_4$ | Cl | 0.50 | 0.10 | 0.5 | 0.63 |
| 4-F—$C_6H_4$ | 4-F—$C_6H_4$ | Cl | 0.16 | 0.035 | 0.06 | 0.07 |
| 4-Cl—$C_6H_4$ | 4-Cl—$C_6H_4$ | Cl | — | — | — | 2.5 |

Anti-apomorphine-activity in dogs: $PD_{50}$-value in mg/kg

TABLE II

Compounds of the formula:

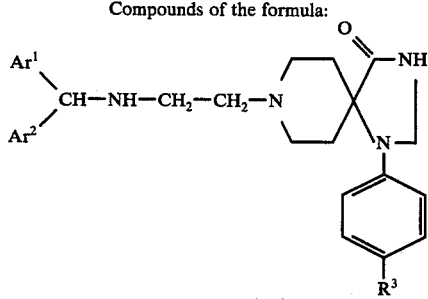

| Ar¹ | Ar² | R³ | 1 hour s.c. | 4 hours s.c. | 16 hours s.c. | 4 hours oral |
|---|---|---|---|---|---|---|
| $C_6H_5$ | $C_6H_5$ | H | 0.06 | 0.10 | 0.25 | — |
| $C_6H_5$ | 4-$CH_3$—$C_6H_4$ | H | 0.015 | 0.015 | 0.07 | — |
| $C_6H_5$ | 3-$CF_3$—$C_6H_4$ | H | 1.0 | 0.20 | — | 2.0 |
| 4-F—$C_6H_4$ | 4-F—$C_6H_4$ | H | 0.015 | 0.008 | 0.03 | — |
| $C_6H_5$ | 3-Cl—$C_6H_4$ | F | 0.10 | 0.015 | 0.06 | 1.0 |
| $C_6H_5$ | 2,3-$(CH_3)_2$—$C_6H_3$ | F | — | 0.50 | — | — |
| 4-F—$C_6H_4$ | 4-F—$C_6H_4$ | F | 0.015 | 0.008 | 0.010 | 0.25 |
| 4-Cl—$C_6H_4$ | 4-Cl—$C_6H_4$ | F | — | — | — | 1.25 |

Anti-apomorphine-activity in dogs: $PD_{50}$ in mg/kg

The following examples are intended to illustrate but not to limit the scope of the present invention. Unless otherwise stated all parts therein are by weight.

EXAMPLE I

To a stirred mixture of 40 parts of sulfinyl chloride in 150 parts of trichloromethane is added dropwise a solution of 64 parts of α-phenyl-3-(trifluoromethyl)benzenemethanol in 375 parts of trichloromethane. Upon completion, stirring is continued for 1 hour at room temperature. The whole is heated to reflux and stirring is continued for 3 hours at reflux temperature. After stirring overnight at room temperature, the solvent is evaporated. The residue is taken up in methylbenzene and the latter is evaporated again, yielding 70 parts (100%) of 1-(chlorophenylmethyl)-3-(trifluoromethyl)benzene as an oily residue.

A mixture of 70 parts of 1-(chlorophenylmethyl)-3-(trifluoromethyl)benzene and 250 parts of 2-aminoethanol is stirred for 3 hours at 140° C. The reaction mixture is cooled and poured onto water. The product is extracted with 4-methyl-2-pentanone. The extract is dried, filtered and evaporated. The residue is purified by column-chromatography over silica gel using a mixture of trichloromethane and methanol (95:5 by volume) as eluent. The pure fractions are collected and the eluent is evaporated, yielding 60 parts (82%) of 2-[{phenyl[3-(trifluoromethyl)phenyl]methyl}amino]ethanol as a residue.

To a stirred and cooled (5°–10° C) mixture of 60 parts of 2-[{phenyl[3-(trifluoromethyl)phenyl]methyl}·amino]-ethanol and 540 parts of methylbenzene are added dropwise 40 parts of sulfinyl chloride. Upon completion, stirring is continued first till room temperature is reached and further overnight at reflux temperature. The reaction mixture is concentrated to one third its volume. After cooling to 10° C, the solid product is filtered off, washed with 2,2'-oxybispropane and dried in vacuo at 75° C, yielding 28.5 parts (40%) of N-(2-chloroethyl)-α-phenyl-3-(trifluoromethyl)benzenemethanamine hydrochloride; mp. 187° C.

EXAMPLE II

Following the procedure of Example I and using equivalent amounts of the appropriate starting materials the following N-(2-chloroethyl)-diarylmethanamine hydrochloride salts are obtained.

$$\begin{array}{c}Ar^1\\ \diagdown\\ \phantom{Ar^2}CH-NH-CH_2-CH_2-Cl\ HCl\\ \diagup\\ Ar^2\end{array}$$

| Ar¹ | Ar² | Melting Point |
|---|---|---|
| C₆H₅ | 3-Cl—C₆H₄ | 228.5° C |
| 4-F—C₆H₄ | 4-F—C₆H₄ | — |
| C₆H₅ | 4-CH₃—C₆H₄ | — |
| 4-Cl—C₆H₄ | 4-Cl—C₆H₄ | — |
| C₆H₅ | 2,5-(CH₃)₂—C₆H₃ | 220° C |
| C₆H₅ | 2,3-(CH₃)₂—C₆H₃ | 220° C |

EXAMPLE III

Following the procedure of Example I and using an equivalent amount of 3-aminopropanol in place of the 2-aminoethanol used therein, the following N-(3-chloropropyl)-diarylamines are obtained:

N-(3-chloropropyl)-α-phenyl-3-(trifluoromethyl)benzenemethanamine;

3-chloro-N-(3-chloropropyl)-α-phenylbenzenemethanamine;

N-(3-chloropropyl)-4-methyl-α-phenylbenzenemethanamine;

4-chloro-N-(3-chloropropyl)-α-(4-chlorophenyl)benzenemethanamine; and

N-(3-chloropropyl)-2,5-dimethyl-α-phenylbenzenemethanamine.

EXAMPLE IV

A mixture of 10 parts of N-(2-chloroethyl)-4-fluoro-α-(4-fluorophenyl)benzenemethanamine hydrochloride, 7.3 parts of 5-chloro-1,3-dihydro-1-(4-piperidinyl)-2H-benzimidazol-2-one, 10.6 parts of sodium carbonate, 0.1 parts of potassium iodide and 80 parts of 4-methyl-2-pentanone is stirred and refluxed overnight. Water is added to the reaction mixture. The precipitated product is filtered off and set aside. From the filtrate, the organic phase is separated, washed with water, dried, filtered and evaporated. The residue is stirred in 4-methyl-2-pentanone. The solid product is filtered off, combined with the precipitated product, obtained above, and crystallized from 4-methyl-2-pentanone. The product is filtered off and dried in vacuo at 95° C, yielding 5 parts of 1-{1-[2-{[bis(4-fluorophenyl)methyl]amino}ethyl]-4-piperidinyl}-5-chloro-1,3-dihydro-2H-benzimidazol-2-one; mp. 198.6° C.

EXAMPLE V

Following the procedure of Example IV and using equivalent amounts of the appropriate starting materials, the following compounds are obtained in free base form or in the form of an acid addition salt after treatment of the free base with the appropriate acid:

| Ar¹ | Ar² | R¹ | Base or Salt form | Melting Point in ° C |
|---|---|---|---|---|
| C₆H₅ | C₆H₅ | Cl | base | 155.9 |
| C₆H₅ | 4-CH₃—C₆H₄ | Cl | base | 169.4 |
| 4-Cl—C₆H₄ | 4-Cl—C₆H₄ | H | base | 224.6 |
| 4-Cl—C₆H₄ | 4-Cl—C₆H₄ | Cl | base | 192.6 |
| C₆H₅ | 3-Cl—C₆H₄ | Cl | base | 139.3 |
| C₆H₅ | 3-Cl—C₆H₄ | H | base | 178.6 |
| C₆H₅ | 4-CH₃—C₆H₄ | H | base | 189.3 |
| C₆H₅ | 2,3-(CH₃)₂—2,5-(CH₃)C₆H₃ | Cl | base | 155.9 |
| C₆H₅ | 2,5-(CH₃)₂—C₆H₃ | H | base | 141.8 |
| C₆H₅ | 3-CF₃—C₆H₄ | H | base | 152 |
| C₆H₅ | 3-CF₃—C₆H₄ | Cl | (E)-2-butenedioate (1:1) | 227.5 |

EXAMPLE VI

A mixture of 8 parts of N-(2-chloroethyl)-4-fluoro-α-(4-fluorophenyl)benzenemethanamine hydrochloride, 5.7 parts of 1-(4-fluorophenyl)-1,3,8-triazaspiro[4,5]decan-4-one, 10 parts of sodium carbonate, 0.1 parts of potassium iodide and 80 parts of 4-methyl-2-pentanone is stirred and refluxed overnight. The reaction mixture is taken up in water and after stirring for a while, the precipitated product is filtered off. The product is washed with 4-methyl-2-pentanone, dried and crystallized from 4-methyl-2-pentanone (activated charcoal). It is filtered off and dried, yielding 4 parts of 8-[2-{[bis(4-fluorophenyl)methyl]amino}ethyl]-1-(4-fluorophenyl)-1,3,8-triazaspiro[4,5]decan-4-one; mp. 193° C.

EXAMPLE VII

Following the procedure of Example VI and using equivalent amounts of the appropriate starting materials the following compounds are prepared:

| Ar¹ | Ar² | R³ | Melting Point in ° C |
|---|---|---|---|
| C₆H₅ | C₆H₅ | H | 183.6 |
| 4-F—C₆H₄ | 4-F—C₆H₄ | H | 192.5 |
| C₆H₅ | 4-CH₃—C₆H₄ | H | 176 |
| 4-Cl—C₆H₄ | 4-Cl—C₆H₄ | F | 217.8 |
| C₆H₅ | 3-Cl—C₆H₄ | H | 169.9 |
| C₆H₅ | 3-Cl—C₆H₄ | F | 180.5 |
| C₆H₅ | 2,5-(CH₃)₂—C₆H₃ | H | 163.8 |
| C₆H₅ | 2,3-(CH₃)₂—C₆H₃ | F | 147.1 |
| C₆H₅ | 2,5-(CH₃)₂—C₆H₃ | H | 177.9 |
| C₆H₅ | 2,3-(CH₃)₂—C₆H₃ | H | 159.3 |
| 4-Cl—C₆H₄ | 4-Cl—C₆H₄ | H | 182.6 (hemihydrate) |

-continued

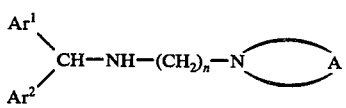

| Ar¹ | Ar² | R³ | Melting Point in °C |
|---|---|---|---|
| C₆H₅ | 3-CF₃—C₆H₄ | H | 154.3 |

EXAMPLE VIII

A mixture of 10 parts of N-(2-chloroethyl)-α-phenylbenzenemethanamine hydrochloride 7 parts of 4-(4-chlorophenyl)-4-piperidinol, 10.6 parts of sodium carbonate, 0.1 parts of potassium iodide and 80 parts of 4-methyl-2-pentanone is stirred and refluxed overnight. The reaction mixture is taken up in water and the layers are separated. The aqueous phase is extracted with 4-methyl--pentanone. The combined organic phases are washed with water, dried, filtered and evaporated. The residue is purified by column-chromatography over silica gel using a mixture of trichloromethane and methanol (96:4 by volume) as eluent. The pure fractions are collected and the eluent is evaporated. The residue is crystallized from a mixture of methylbenzene and 2,2'-oxybispropane. The product is filtered off and dried, yielding 4.5 parts of 4-(4-chlorophenyl)-1-{2-[(diphenylmethyl)amino]ethyl}-4-piperidinol; mp. 113.9° C.

EXAMPLE IX

Following the procedure of Example VIII there is prepared 1-[2-{[bis(4-fluorophenyl)methyl]amino}ethyl]-4-(4-chlorophenyl)-4-piperidinol dihydrochloride; mp. 208.3° C. by the reaction of N-(2-chloroethyl)-4-fluoro-α-(4-fluorophenyl)benzenemethanamine hydrochloride with 4-(4-chlorophenyl)-4-piperidinol.

EXAMPLE X

In a similar manner as described in Examples IV, VI and VII the following compounds are obtained by the reaction of an appropriate N-(3-chloropropyl)-diarylmethanamine with an appropriate piperidine derivative of formula (III):

1-{1-[3-{[bis(4-fluorophenyl)methyl]amino}propyl]-4-piperidinyl}-5-chloro-1,3-dihydro-2H-benzimidazol-2-one;
5-chloro-1-[1-{3-[(diphenylmethyl)amino]propyl}-4-piperidinyl]-1,3-dihydro-2H-benzimidazol-2-one;
5-chloro-1-{1-[3-{[(3-chlorophenyl)phenylmethyl]amino}-propyl]-4-piperidinyl}-1,3-dihydro-2H-benzimidazol-2-one;
1,3-dihydro-1-{1-[3-{[(4-methylphenyl)phenylmethyl]amino}-propyl]-4-piperidinyl}-2H-benzimidazol-2-one;
1-{1-[3-{[bis(4-chlorophenyl)methyl]amino}propyl]-4-piperidinyl}-1,3-dihydro-2H-benzimidazol-2-one;
8-{3-[(diphenylmethyl)amino]propyl}-1-phenyl-1,3,8-triazaspiro[4,5]decan-4-one;
8-[3-{[bis(4-fluorophenyl)methyl]amino}propyl]-1-(4-fluorophenyl)-1,3,8-triazaspiro[4,5]decan-4-one;
8-[3-{[bis(4-chlorophenyl)methyl]amino}propyl]-1-(4-fluorophenyl)-1,3,8-triazaspiro[4,5]decan-4-one;
8-[3-{[(2,5-dimethylphenyl)phenylmethyl]amino}•propyl]-1-phenyl-1,3,8-triazaspiro[4,5]decan-4-one;
4-(4-chlorophenyl)-1-{3-[(diphenylmethyl)amino]-propyl}4-piperidinol; and
1-[3-{[bis(4-fluorophenyl)methyl]amino}propyl]-4-(4-chlorophenyl)-4-piperidinol.

We claim:
1. A chemical compound selected from the group consisting of a piperidine derivative having the formula

and the pharmaceutically acceptable acid addition salts thereof, wherein:

Ar¹ and Ar² are each independently selected from the group consisting of phenyl and substituted phenyl, said substituted phenyl being phenyl having from 1 to 2 substituents independently selected from the group consisting of halo, lower alkyl, lower alkyloxy and trifluoromethyl;

n is the integer 2 or 3; and the radical $$-N\bigcirc A$$

is a member selected from the group consisting of the following:

a. a radical of the formula

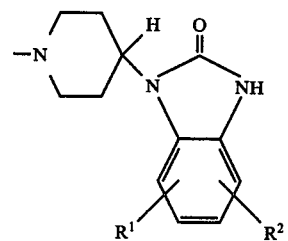

wherein R¹ and R² are each independently selected from the group consisting of hydrogen, halo, lower alkyl and lower alkyloxy;

b. a radical of the formula

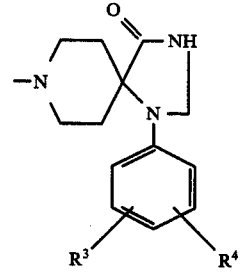

wherein R³ and R⁴ are each independently selected from the group consisting of hydrogen, halo, lower alkyl, lower alkyloxy and trifluoromethyl; and c. a radical of the formula

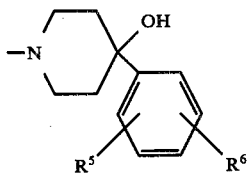

wherein R⁵ is selected from the group consisting of hydrogen and methyl; and R⁶ is selected from the group consisting of hydrogen, halo, lower alkyl and trifluoromethyl.

2. A chemical compound selected from the group consisting of 1-{1-[2-{[bis(4-fluorophenyl)methyl]amino}-ethyl]-4-piperidinyl}-5-chloro-1,3-dihydro-2H-benzimidazol-2-one and the pharmaceutically acceptable acid addition salts thereof.

3. A chemical compound selected from the group consisting of 8-[2-{[(4-methylphenyl)phenylmethyl]amino}ethyl]-1-phenyl-1,3,8-triazaspiro[4,5]decan-4-one and the pharmaceutically acceptable acid addition salts thereof.

4. A chemical compound selected from the group consisting of 8-[2-{[bis(4-fluorophenyl)methyl]amino}ethyl]-1-phenyl-1,3,8-triazaspiro[4,5]decan-4-one and the pharmaceutically acceptable acid addition salts thereof.

5. A chemical compound selected from the group consisting of 8-[2-{[bis(4-fluorophenyl)methyl]amino}ethyl]-1-(4-fluorophenyl)-1,3,8-triazaspiro[4,5]decan-4-one and the pharmaceutically acceptable acid addition salts thereof.

* * * * *

UNITED STATES PATENT AND TRADEMARK OFFICE
CERTIFICATE OF CORRECTION

PATENT NO. : 4,082,755
DATED : April 4, 1978
INVENTOR(S) : Ineke van Wijngaarden; Willem Soudijn; Jan Vandenberk and Jozef Fr. Hens It is certified that error appears in the above-identified patent and that said Letters Patent are hereby corrected as shown below:

On the cover and at Page 1, "Piperidimes" should be
       -- Piperidines --.
At Column 2, Line 63, "indicating" should be -- indicated --.
At Column 9, Line 27, "methyl-pentanone" should be
       -- methyl-2-pentanone --.
At Column 9, Line 49, "VI and VII" should be -- VI and VIII --.

Signed and Sealed this

Fourteenth Day of November 1978

[SEAL]

Attest:

RUTH C. MASON
*Attesting Officer*

DONALD W. BANNER
*Commissioner of Patents and Trademarks*